United States Patent
Monia et al.

(12)

(10) Patent No.: US 6,309,882 B1
(45) Date of Patent: Oct. 30, 2001

(54) ANTISENSE INHIBITION OF REPLICATION PROTEIN A P70 SUBUNIT

(75) Inventors: Brett P. Monia, LaCosta, CA (US); James P. Basilion, Brookline; Vincent P. Stanton, Jr., Belmont, both of MA (US)

(73) Assignees: ISIS Pharmaceuticals, Inc., Carlsbad, CA (US); Variagenics, Inc., Cambridge, MA (US)

( * ) Notice: Subject to any disclaimer, the term of this patent is extended or adjusted under 35 U.S.C. 154(b) by 0 days.

(21) Appl. No.: 09/393,529

(22) Filed: Sep. 10, 1999

(51) Int. Cl.[7] ............... C07H 21/02; C07H 21/04; C12Q 1/68; C12N 15/85; C12K 15/86

(52) U.S. Cl. ............... 435/375; 435/325; 435/91.1; 435/6; 536/23.1; 536/24.5; 536/24.3; 536/24.31; 536/24.33

(58) Field of Search ............... 435/6, 91.1, 91.3, 435/357, 375, 325; 536/23.1, 23.2, 24.5, 24.3, 24.31, 24.33; 514/44

(56) References Cited

U.S. PATENT DOCUMENTS

| | | | |
|---|---|---|---|
| 5,702,890 | 12/1997 | Housman | 435/6 |
| 5,801,154 * | 9/1998 | Baracchine et al. | 514/44 |

FOREIGN PATENT DOCUMENTS

WO 98/41648    9/1998    (WO) .

OTHER PUBLICATIONS

James, Antiviral Chemistry and Chemotherapy (1991) 2(4), p 191–214 1991.*

Milner et al., Nature Biotechnology, V 15, p 537–541. Jun. 1997.*

Basilion et al., Molecular Phrmacology, 56:359–369 Aug. 1999.*

Branch et al., TIBS23, p45–50. Feb. 1998.*

Crooke, Antisense research and Application, p1–50. Jul. 1998.*

Erdile et al., Journal of Biological Chemistry, vol. 266, p12090–12098. Jun. 25, 1991.*

Erdile et al., "Characterization of a cDNA Encoding the 70–kDa Single–stranded DNA–binding Subunit of Human Replication Protein A and the Role of the Protein in DNA Replication", J. Biol. Chem 1991 266, 12090–12098.

Rodriquez[1], et al., "Genetic Changes in Epithelial Solid Neoplasia", Cancer Res.1994 54, 3398–3403.

* cited by examiner

*Primary Examiner*—Sean McGarry
*Assistant Examiner*—Karen A. Lacourciere
(74) *Attorney, Agent, or Firm*—Licata & Tyrrell P.C.

(57) ABSTRACT

Compositions and methods are provided for modulating the expression of the replication protein A p70 subunit and for the treatment and diagnosis of diseases associated with replication protein A p70 subunit.

13 Claims, No Drawings

SEQUENCE LISTING

```
<160> NUMBER OF SEQ ID NOS: 18

<210> SEQ ID NO 1
<211> LENGTH: 2393
<212> TYPE: DNA
<213> ORGANISM: Homo sapiens
<220> FEATURE:
<221> NAME/KEY: CDS
<222> LOCATION: (70)..(1920)
<300> PUBLICATION INFORMATION:
<303> JOURNAL: J. Biol. Chem.
<304> VOLUME: 266
<305> ISSUE: 18
<306> PAGES: 12090-12098
<307> DATE: 1991-06-25
<308> DATABASE ACCESSION NUMBER: M63488/Genbank
<309> DATABASE ENTRY DATE: 1993-11-01

<400> SEQUENCE: 1
cggcgcggga cccgggtggg gaagctggag ctgttgcggg gtccgcgggg aagtcttggc      60 ggtggagcc atg gtc ggc cag ctg agc gag ggg gcc att gcg gcc atc atg    111
          Met Val Gly Gln Leu Ser Glu Gly Ala Ile Ala Ala Ile Met
            1               5                  10 cag aag ggg gat aca aac ata aag ccc atc ctc caa gtc atc aac atc    159
Gln Lys Gly Asp Thr Asn Ile Lys Pro Ile Leu Gln Val Ile Asn Ile
 15                  20                  25                  30 cgt ccc att act acg ggg aat agt ccg ccg cgt tat cga ctg ctc atg    207
Arg Pro Ile Thr Thr Gly Asn Ser Pro Pro Arg Tyr Arg Leu Leu Met
                 35                  40                  45 agt gat gga ttg aac act cta tcc tct ttc atg ttg gcg aca cag ttg    255
Ser Asp Gly Leu Asn Thr Leu Ser Ser Phe Met Leu Ala Thr Gln Leu
```

-continued

```
                    50                      55                      60
aac cct ctc gtg gag gaa gaa caa ttg tcc agc aac tgt gta tgc cag        303
Asn Pro Leu Val Glu Glu Glu Gln Leu Ser Ser Asn Cys Val Cys Gln
             65                      70                      75 att cac aga ttt att gtg aac act ctg aaa gac gga agg aga gta gtt        351
Ile His Arg Phe Ile Val Asn Thr Leu Lys Asp Gly Arg Arg Val Val
         80                      85                      90 atc ttg atg gaa tta gaa gtt ttg aag tca gct gaa gca gtt gga gtg        399
Ile Leu Met Glu Leu Glu Val Leu Lys Ser Ala Glu Ala Val Gly Val
 95                     100                     105                     110 aag att ggc aat cca gtg ccc tat aat gaa gga ctc ggg cag ccg caa        447
Lys Ile Gly Asn Pro Val Pro Tyr Asn Glu Gly Leu Gly Gln Pro Gln
                    115                     120                     125 gta gct cct cca gcg cca gca gcc agc cca gca gca agc agc agg ccc        495
Val Ala Pro Pro Ala Pro Ala Ala Ser Pro Ala Ala Ser Ser Arg Pro
             130                     135                     140 cag ccg cag aat gga agc tcg gga atg ggt tct act gtt tct aag gct        543
Gln Pro Gln Asn Gly Ser Ser Gly Met Gly Ser Thr Val Ser Lys Ala
         145                     150                     155 tat ggt gct tca aag aca ttt gga aaa gct gca ggt ccc agc ctg tca        591
Tyr Gly Ala Ser Lys Thr Phe Gly Lys Ala Ala Gly Pro Ser Leu Ser
 160                     165                     170 cac act tct ggg gga aca cag tcc aaa gtg gtg ccc att gcc agc ctc        639
His Thr Ser Gly Gly Thr Gln Ser Lys Val Val Pro Ile Ala Ser Leu
175                     180                     185                     190 act cct tac cag tcc aag tgg acc att tgt gct cgt gtt acc aac aaa        687
Thr Pro Tyr Gln Ser Lys Trp Thr Ile Cys Ala Arg Val Thr Asn Lys
                    195                     200                     205 agt cag atc cgt acc tgg agc aac tcc cga ggg gaa ggg aag ctt ttc        735
Ser Gln Ile Arg Thr Trp Ser Asn Ser Arg Gly Glu Gly Lys Leu Phe
             210                     215                     220 tcc cta gaa ctg gtt gac gaa agt ggt gaa atc cga gct aca gct ttc        783
Ser Leu Glu Leu Val Asp Glu Ser Gly Glu Ile Arg Ala Thr Ala Phe
         225                     230                     235 aat gag caa gtg gac aag ttc ttt cct ctt att gaa gtg aac aag gtg        831
Asn Glu Gln Val Asp Lys Phe Phe Pro Leu Ile Glu Val Asn Lys Val
 240                     245                     250 tat tat ttc tcg aaa ggc acc ctg aag att gct aac aag cag ttc aca        879
Tyr Tyr Phe Ser Lys Gly Thr Leu Lys Ile Ala Asn Lys Gln Phe Thr
255                     260                     265                     270 gct gtt aaa aat gac tac gag atg acc ttc aat aac gag act tcc gtc        927
Ala Val Lys Asn Asp Tyr Glu Met Thr Phe Asn Asn Glu Thr Ser Val
                    275                     280                     285 atg ccc tgt gag gac gac cat cat tta cct acg gtt cag ttt gat ttc        975
Met Pro Cys Glu Asp Asp His His Leu Pro Thr Val Gln Phe Asp Phe
             290                     295                     300 acg ggg att gat gac ctc gag aac aag tcg aaa gac tca ctt gta gac       1023
Thr Gly Ile Asp Asp Leu Glu Asn Lys Ser Lys Asp Ser Leu Val Asp
         305                     310                     315 atc atc ggg atc tgc aag agc tat gaa gac gcc act aaa atc aca gtg       1071
Ile Ile Gly Ile Cys Lys Ser Tyr Glu Asp Ala Thr Lys Ile Thr Val
 320                     325                     330 agg tct aac aac aga gaa gtt gcc aag agg aat atc tac ttg atg gac       1119
Arg Ser Asn Asn Arg Glu Val Ala Lys Arg Asn Ile Tyr Leu Met Asp
335                     340                     345                     350 aca tcc ggg aag gtg gtg act gct aca ctg tgg ggg gaa gat gct gat       1167
Thr Ser Gly Lys Val Val Thr Ala Thr Leu Trp Gly Glu Asp Ala Asp
                    355                     360                     365 aaa ttt gat ggt tct aga cag ccc gtg ttg gct atc aaa gga gcc cga       1215
```

-continued

```
                    Lys Phe Asp Gly Ser Arg Gln Pro Val Leu Ala Ile Lys Gly Ala Arg
                                        370                 375                 380 gtc tct gat ttc ggt gga cgg agc ctc tcc gtg ctg tct tca agc act                    1263
Val Ser Asp Phe Gly Gly Arg Ser Leu Ser Val Leu Ser Ser Ser Thr
        385                 390                 395 atc att gcg aat cct gac atc cca gag gcc tat aag ctt cgt gga tgg                    1311
Ile Ile Ala Asn Pro Asp Ile Pro Glu Ala Tyr Lys Leu Arg Gly Trp
    400                 405                 410 ttt gac gca gaa gga caa gcc tta gat ggt gtt tcc atc tct gat cta                    1359
Phe Asp Ala Glu Gly Gln Ala Leu Asp Gly Val Ser Ile Ser Asp Leu
415                 420                 425                 430 aag agc ggc gga gtc gga ggg agt aac acc aac tgg aaa acc ttg tat                    1407
Lys Ser Gly Gly Val Gly Gly Ser Asn Thr Asn Trp Lys Thr Leu Tyr
                435                 440                 445 gag gtc aaa tcc gag aac ctg ggc caa ggc gac aag ccg gac tac ttt                    1455
Glu Val Lys Ser Glu Asn Leu Gly Gln Gly Asp Lys Pro Asp Tyr Phe
            450                 455                 460 agt tct gtg gcc aca gtg gtg tat ctt cgc aaa gag aac tgc atg tac                    1503
Ser Ser Val Ala Thr Val Val Tyr Leu Arg Lys Glu Asn Cys Met Tyr
        465                 470                 475 caa gcc tgc ccg act cag gac tgc aat aag aaa gtg att gat caa cag                    1551
Gln Ala Cys Pro Thr Gln Asp Cys Asn Lys Lys Val Ile Asp Gln Gln
    480                 485                 490 aat gga ttg tac cgc tgt gag aag tgc gac acc gaa ttt ccc aat ttc                    1599
Asn Gly Leu Tyr Arg Cys Glu Lys Cys Asp Thr Glu Phe Pro Asn Phe
495                 500                 505                 510 aag tac cgc atg atc ctg tca gta aat att gca gat ttt caa gag aat                    1647
Lys Tyr Arg Met Ile Leu Ser Val Asn Ile Ala Asp Phe Gln Glu Asn
                515                 520                 525 cag tgg gtg act tgt ttc cag gag tct gct gaa gct atc ctt gga caa                    1695
Gln Trp Val Thr Cys Phe Gln Glu Ser Ala Glu Ala Ile Leu Gly Gln
            530                 535                 540 aat gct gct tat ctt ggg gaa tta aaa gac aag aat gaa cag gca ttt                    1743
Asn Ala Ala Tyr Leu Gly Glu Leu Lys Asp Lys Asn Glu Gln Ala Phe
        545                 550                 555 gaa gaa gtt ttc cag aat gcc aac ttc cga tct ttc ata ttc aga gtc                    1791
Glu Glu Val Phe Gln Asn Ala Asn Phe Arg Ser Phe Ile Phe Arg Val
    560                 565                 570 agg gtc aaa gtg gag acc tac aac gac gag tct cga att aag gcc act                    1839
Arg Val Lys Val Glu Thr Tyr Asn Asp Glu Ser Arg Ile Lys Ala Thr
575                 580                 585                 590 gtg atg gac gtg aag ccc gtg gac tac aga gag tat ggc cga agg ctg                    1887
Val Met Asp Val Lys Pro Val Asp Tyr Arg Glu Tyr Gly Arg Arg Leu
                595                 600                 605 gtc atg agc atc agg aga agt gca ttg atg tga gaggagcagt gccaatcggg                  1940
Val Met Ser Ile Arg Arg Ser Ala Leu Met
            610                 615 cagaagtttg caaataggca gaatggaatc gatttcctcc cacctccgtg tgacgatccc                  2000
atgttagcta cacagtgcag aggctcttga tggtggacta agcaattcct ccctcgtgcg                  2060
catctcagaa cccatcggta ggcaaaggaa aatacgctca ggtggttgtg gtgtagactg                  2120
tgtcaggcct acggagtcag ccagtggcta gcgcaagacc agtcactccc tctgccttca                  2180
ggcttctgtc aatttcatta tcatcaagca ggaattatgt cgtaagtcac tgaccctaac                  2240
tgcagaccat gaagtaaatt atgtaactag gttttttgctt ctccagtggt gaccacccccc               2300 ccccatcccc gctcacaact tgggttcttc tcagcggggc gagctgagaa gcggtcatga                  2360
gcacctgggg attttagtaa gtgtgtcttc cta                                                2393
```

-continued

```
<210> SEQ ID NO 2
<211> LENGTH: 616
<212> TYPE: PRT
<213> ORGANISM: Homo sapiens

<400> SEQUENCE: 2

Met Val Gly Gln Leu Ser Glu Gly Ala Ile Ala Ile Met Gln Lys
  1               5                  10                  15

Gly Asp Thr Asn Ile Lys Pro Ile Leu Gln Val Ile Asn Ile Arg Pro
                 20                  25                  30

Ile Thr Thr Gly Asn Ser Pro Arg Tyr Arg Leu Leu Met Ser Asp
                 35                  40                  45

Gly Leu Asn Thr Leu Ser Ser Phe Met Leu Ala Thr Gln Leu Asn Pro
 50                  55                  60

Leu Val Glu Glu Gln Leu Ser Ser Asn Cys Val Cys Gln Ile His
 65                  70                  75                  80

Arg Phe Ile Val Asn Thr Leu Lys Asp Gly Arg Arg Val Val Ile Leu
                 85                  90                  95

Met Glu Leu Glu Val Leu Lys Ser Ala Glu Ala Val Gly Val Lys Ile
                100                 105                 110

Gly Asn Pro Val Pro Tyr Asn Glu Gly Leu Gly Gln Pro Gln Val Ala
                115                 120                 125

Pro Pro Ala Pro Ala Ala Ser Pro Ala Ala Ser Ser Arg Pro Gln Pro
130                 135                 140

Gln Asn Gly Ser Ser Gly Met Gly Ser Thr Val Ser Lys Ala Tyr Gly
145                 150                 155                 160

Ala Ser Lys Thr Phe Gly Lys Ala Ala Gly Pro Ser Leu Ser His Thr
                165                 170                 175

Ser Gly Gly Thr Gln Ser Lys Val Val Pro Ile Ala Ser Leu Thr Pro
                180                 185                 190

Tyr Gln Ser Lys Trp Thr Ile Cys Ala Arg Val Thr Asn Lys Ser Gln
                195                 200                 205

Ile Arg Thr Trp Ser Asn Ser Arg Gly Glu Gly Lys Leu Phe Ser Leu
                210                 215                 220

Glu Leu Val Asp Glu Ser Gly Glu Ile Arg Ala Thr Ala Phe Asn Glu
225                 230                 235                 240

Gln Val Asp Lys Phe Phe Pro Leu Ile Glu Val Asn Lys Val Tyr Tyr
                245                 250                 255

Phe Ser Lys Gly Thr Leu Lys Ile Ala Asn Lys Gln Phe Thr Ala Val
                260                 265                 270

Lys Asn Asp Tyr Glu Met Thr Phe Asn Asn Glu Thr Ser Val Met Pro
                275                 280                 285

Cys Glu Asp Asp His His Leu Pro Thr Val Gln Phe Asp Phe Thr Gly
                290                 295                 300

Ile Asp Asp Leu Glu Asn Lys Ser Lys Asp Ser Leu Val Asp Ile Ile
305                 310                 315                 320

Gly Ile Cys Lys Ser Tyr Glu Asp Ala Thr Lys Ile Thr Val Arg Ser
                325                 330                 335

Asn Asn Arg Glu Val Ala Lys Arg Asn Ile Tyr Leu Met Asp Thr Ser
                340                 345                 350

Gly Lys Val Val Thr Ala Thr Leu Trp Gly Glu Asp Ala Asp Lys Phe
                355                 360                 365

Asp Gly Ser Arg Gln Pro Val Leu Ala Ile Lys Gly Ala Arg Val Ser
                370                 375                 380
```

-continued

```
Asp Phe Gly Gly Arg Ser Leu Ser Val Leu Ser Ser Thr Ile Ile
385                 390                 395                 400

Ala Asn Pro Asp Ile Pro Glu Ala Tyr Lys Leu Arg Gly Trp Phe Asp
            405                 410                 415

Ala Glu Gly Gln Ala Leu Asp Gly Val Ser Ile Ser Asp Leu Lys Ser
        420                 425                 430

Gly Gly Val Gly Gly Ser Asn Thr Asn Trp Lys Thr Leu Tyr Glu Val
    435                 440                 445

Lys Ser Glu Asn Leu Gly Gln Gly Asp Lys Pro Asp Tyr Phe Ser Ser
450                 455                 460

Val Ala Thr Val Val Tyr Leu Arg Lys Glu Asn Cys Met Tyr Gln Ala
465                 470                 475                 480

Cys Pro Thr Gln Asp Cys Asn Lys Lys Val Ile Asp Gln Gln Asn Gly
            485                 490                 495

Leu Tyr Arg Cys Glu Lys Cys Asp Thr Glu Phe Pro Asn Phe Lys Tyr
        500                 505                 510

Arg Met Ile Leu Ser Val Asn Ile Ala Asp Phe Gln Glu Asn Gln Trp
    515                 520                 525

Val Thr Cys Phe Gln Glu Ser Ala Glu Ala Ile Leu Gly Gln Asn Ala
530                 535                 540

Ala Tyr Leu Gly Glu Leu Lys Asp Lys Asn Glu Gln Ala Phe Glu Glu
545                 550                 555                 560

Val Phe Gln Asn Ala Asn Phe Arg Ser Phe Ile Phe Arg Val Arg Val
            565                 570                 575

Lys Val Glu Thr Tyr Asn Asp Glu Ser Arg Ile Lys Ala Thr Val Met
        580                 585                 590

Asp Val Lys Pro Val Asp Tyr Arg Glu Tyr Gly Arg Arg Leu Val Met
    595                 600                 605

Ser Ile Arg Arg Ser Ala Leu Met
    610                 615

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
cccacccggg tcccgcgccg                                                   20

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
gaccatggct ccaccgccaa                                                   20

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
```
tggccgacca tggctccacc                                                     20

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
tagcttcagc agactcctgg                                                     20

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
tgatgctcat gaccagcctt                                                     20

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
actgctcctc tcacatcaat                                                     20

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
gattccattc tgcctatttg                                                     20

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
ctgcactgtg tagctaacat                                                     20

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
gcacgaggga ggaaattgct                                                     20

<210> SEQ ID NO 12
<211> LENGTH: 20
<212> TYPE: DNA

-continued

```
<213> ORGANISM: Artificial Sequence
<220> FEATURE:
<223> OTHER INFORMATION: Synthetic

<400> SEQUENCE: 12
gagcgtattt tcctttgcct                                               20

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
cagagggagt gactggtctt                                               20

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
tgacttacga cataattcct                                               20

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
tggtctgcag ttagggtcag                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
atgggggggg gtggtcacca                                               20

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
tagcttcagc ggactcctgg                                               20

<210> SEQ ID NO 18
<211> LENGTH: 18
<212> TYPE: DNA
<213> ORGANISM: Artificial Sequence
```

-continued

```
<220> FEATURE:
<223> OTHER INFORMATION: Synthetic

<400> SEQUENCE: 18
gcttcagcgg actcctgg                                            18
```

ANTISENSE INHIBITION OF REPLICATION PROTEIN A P70 SUBUNIT

FIELD OF THE INVENTION

This invention relates to compositions and methods for modulating expression of the replication protein A 70 kDa subunit gene, a naturally present cellular gene encoding a subunit of a complex implicated in multiple processes of DNA metabolism. These compositions and methods can be used diagnostically or therapeutically. Furthermore, this invention is directed to treatment of cancer via specific inhibition of the replication protein A 70 kDa subunit gene.

BACKGROUND OF THE INVENTION

Human replication protein A (RPA), also human single-stranded DNA-binding protein (HSSB), is a single-stranded DNA-binding protein that also interacts and regulates the function of a number of other cellular proteins. This heterotrimeric protein is composed of three subunits, the 70 kDa subunit (RPA70 or p70), p34 (RPA34) and p11 (RPA11) encoded by genes located on different chromosomes (sometimes referred to as RPA1, RPA2 and RPA3 genes, respectively). Each of the three subunits of RPA has been shown to be essential for DNA replication, homologous recombination and nucleotide excision repair in vitro (He, Z., et al., *Nature*, 1995, 374, 566–569), and disruption of any of the three subunits in yeast is lethal (Brill, S. J. and Stillman, B., *Genes and Development*, 1991, 5, 1589–1600).

RPA70 binds to single-stranded DNA and certain double-stranded sequences with high affinity (Lao, Y., et al., *Biochemistry*, 1999, 38, 3974–3984) and possesses unwindase activity. RPA also binds cisplatin (Patrick, S. M., and Turchi, J. J., *Biochemistry*, 1998, 37, 8808–8815) and UV-damaged DNA. In addition to its DNA binding, RPA interacts with various proteins involved in DNA replication, repair, recombination, transcription and cell regulation. RPA70 interacts with DNA polymerase α, during initiation of replication and elongation, and DNA polymerase δ (Longhese, M. P., et al., *Mol. Cell. Biol.*, 1994, 14, 7884–7890). Both RPA70 and RPA34 interact with the Xeroderma Pigmentosum group A complementing protein (XPA) on damaged DNA recruiting endonucleases involved in DNA repair (Stigger, E., et al., J. Biol. Chem., 1998, 273, 9337–9343). RPA also interacts with transcriptional activators including the tumor suppressor gene, p53 (Miller, S. D., et al., *Mol. Cell. Biol.*, 1997, 17, 2194–2201).

The function of the RPA70 subunit has been studied primarily with mutant RPA1 genes (Longhese, M. P., et al., *Mol. Cell. Biol.*, 1994, 14, 7884–7890) and deletion analysis.

RPA70 is believed to be an attractive target for cancer therapeutics. In a preferred embodiment, such a therapy can take advantage of natural genetic variation within the genome in combination with loss of heterozygosity (LOH) in cancer cells. This approach is based on allele-specific targeting and is described in WO 98/41648, herein incorporated by reference in its entirety.

It is estimated that natural genetic variation occurs in approximately one nucleotide in 300 throughout the genome (Cooper, D. N., et al., *Human Genetics*, 1985, 69, 201–205). Because of the large number of polymorphisms or sequence variances found in the human genome, most individuals are heterozygous for one or more sequence variances in genes of normal tissues, including many genes that are essential for cell survival. LOH reduces many of these genes to hemizygosity in cancer cells, eliminating heterozygosity, and creating a large number of absolute genetic differences between tumor and normal cells (Cavenee, W. K., et al., *Mutat. Res.*, 1991, 247, 199–202; Schwechheimer, K. and Cavenee, W. K., *Clin. Investig.*, 1993, 71, 488–502).

An early event in the clonal evolution of cancers is the loss of large chromosomal regions or even whole chromosomes (Lengauer, C., et al., *Nature*, 1998, 396, 643–649). Presumably, these losses are driven, in part, by positive selection for cells in which LOH leads to the loss of tumor suppressor functions. LOH in certain cancers can involve more than 20% of the total genome (Lengauer, C., et al., *Nature*, 1998, 396, 643–649) and it is evident that thousands of genes are also lost from cancer cells due to LOH. Based on current estimates of human gene number this suggests that 15,000 to 20,000 genes, that are not tumor suppressor genes, are also reduced to hemizygosity in cancer cells by LOH. Among these genes are many that are essential for cell survival. The RPA70 gene has been mapped to chromosome 17p13.3 in close proximity to the tumor suppressor gene p53 at position 17p13.1 (Umbricht, C. B., et al., *Genomics*, 1993, 20, 249–257). This segment of the genome is affected by LOH in many common epithelial cancers (Rodriguez, E., et al., *Cancer Res.*, 1994, 54, 3398–3406). Thus, RPA70 represents an attractive target for allele-specific therapy.

By exploiting the absolute genetic differences in RPA70 genes between cancer cells and normal cells that arise as a consequence of normal genetic variation and LOH, RPA70 can be an effective target for cancer therapy. Inhibitors, especially antisense compounds, are identified that inactivate one or more variant forms of the target gene, but not the normal form that is present in the general population. Inhibitors specific for the remaining allele expressed in the cancer cells, when administered to patients, would be selectively toxic to the cancer cells. Normal cells and tissues, which express both the sensitive and insensitive alleles, would escape significant toxicity.

There remains a long-felt need for improved compositions and methods for inhibiting RPA 70 kDa subunit gene expression.

SUMMARY OF THE INVENTION

The present invention provides antisense compounds which are targeted to nucleic acids encoding human replication protein A 70 kDa subunit and are capable of inhibiting replication protein A 70 kDa subunit expression. In preferred embodiments, the antisense compounds are targeted to a variant form of RPA70. The oligonucleotides of the invention are believed to be useful both diagnostically and therapeutically, and are believed to be particularly useful in the methods of the present invention.

The present invention also comprises methods of inhibiting the expression of human replication protein A 70 kDa subunit. These methods are believed to be useful both therapeutically and diagnostically as a consequence of the association between replication protein A 70 kDa subunit inhibition and its essential roles in DNA metabolism and, consequently, cell viability. These methods are also useful as tools, for example, for determining the role of replication protein A 70 kDa subunit expression in various cell functions and physiological processes and conditions and for detecting and diagnosing conditions associated with replication protein A 70 kDa subunit and its variant forms.

Methods of treating cancer are also provided. These methods employ the oligonucleotides of the invention. These methods are believed to be useful both therapeutically and as clinical research and diagnostic tools.

DETAILED DESCRIPTION OF THE INVENTION

Replication protein A is an essential protein that plays a major role in multiple processes in DNA metabolism. It has both DNA binding activity and protein binding activity. The RPA70 subunit is required in many processes involving DNA replication, repair and recombination.

Since natural sequence variations occur within this gene as well as throughout the genome, and LOH at this gene locus is associated with many cancers, the RPA70 gene is an attractive target for cancer therapeutics based on allele-specific targeting. Nucleic acid based therapeutics, such as exemplified by antisense approach, are ideal for this targeting.

The relationship between an antisense compound such as an oligonucleotide and its complementary nucleic acid target, to which it hybridizes, is commonly referred to as "antisense". "Targeting" an oligonucleotide to a chosen nucleic acid target, in the context of this invention, is a multistep process. The process usually begins with identifying a nucleic acid sequence whose function is to be modulated. This may be, as examples, a cellular gene (or mRNA made from the gene) whose expression is associated with a particular disease state, or a foreign nucleic acid from an infectious agent. In the present invention, the target is a nucleic acid encoding RPA70; in other words, a gene encoding RPA70, or mRNA expressed from the RPA70 gene. mRNA which encodes RPA70 is presently the preferred target. The targeting process also includes determination of a site or sites within the nucleic acid sequence for the antisense interaction to occur such that modulation of gene expression will result.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention which are targeted wholly or in part to these associated ribonucleotides as well as to the informational ribonucleotides. The oligonucleotide may therefore be specifically hybridizable with a transcription initiation site region, a translation initiation codon region, a 5' cap region, an intron/exon junction, coding sequences, a translation termination codon region or sequences in the 5'- or 3'-untranslated region. Since, as is known in the art, the translation initiation codon is typically 5'-AUG (in transcribed mRNA molecules; 5'-ATG in the corresponding DNA molecule), the translation initiation codon is also referred to as the "AUG codon,"the "start codon"or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding RPA70, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region," "AUG region" and "translation initiation codon region" refer to a portion of such an mRNA or gene that encompasses from about 25 to about 50 contiguous nucleotides in either direction (i.e., 5' or 3') from a translation initiation codon. This region is a preferred target region. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. This region is a preferred target region. The open reading frame (ORF) or "coding region," which is known in the art to refer to the region between the translation initiation codon and the translation termination codon, is also a region which may be targeted effectively. Other preferred target regions include the 5' untranslated region (5' UTR), known in the art to refer to the portion of an mRNA in the 5' direction from the translation initiation codon, and thus including nucleotides between the 5' cap site and the translation initiation codon of an mRNA or corresponding nucleotides on the gene and the 3' untranslated region (3' UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'—5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a pre-mRNA transcript to yield one or more mature mRNA. The remaining (and therefore translated) regions are known as "exons" and are spliced together to form a continuous mRNA sequence. mRNA splice sites, i.e., exon-exon or intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. Targeting particular exons in alternatively spliced mRNAs may also be preferred. It has also been found that introns can also be effective, and therefore preferred, target regions for antisense compounds targeted, for example, to DNA or pre-mRNA.

Once the target site or sites have been identified, oligonucleotides are chosen which are sufficiently complementary to the target, i.e., hybridize sufficiently well and with sufficient specificity, to give the desired modulation.

"Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them.

"Specifically hybridizable" and "complementary" are terms which are used to indicate a sufficient degree of complementarity such that stable and specific binding occurs between the DNA or RNA target and the oligonucleotide.

It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment and, in the case of in vitro assays, under conditions in which the assays are conducted.

In the context of the present invention, it is particularly desirable to target variances in the RPA70 gene. "Variances" or "variant sequences" are those which differ by at least one nucleotide from the "normal" allele sequences or from other variant alleles. Thus, the antisense compound would be 100% complementary to an allele containing the variant sequence, but not 100% complementary (i.e., differing by at least one nucleotide from absolute complementarity) to the normal gene. For example, it has been found that five variances are common in the RPA70 gene (WO 98/41648). Antisense oligonucleotides targeting these and other RPA70 variances are believed to be therapeutically and diagnostically useful. Regions of the normal RPA70 gene that are amenable to antisense modulation would be expected to be attractive targets for the allele-specific targeting approach.

Hybridization of antisense oligonucleotides with mRNA interferes with one or more of the normal functions of mRNA. The functions of mRNA to be interfered with include all vital functions such as, for example, translocation of the RNA to the site of protein translation, translation of protein from the RNA, splicing of the pre-mRNA to yield one or more mRNA species, and catalytic activity which may be engaged in by the RNA. Binding of specific protein(s) to the RNA may also be interfered with by antisense oligonucleotide hybridization to the RNA.

The overall effect of interference with mRNA function is modulation of expression of RPA70 and, in the context of this invention, ultimately modulation of cellular viability by interference with DNA metabolism, including DNA replication. In the context of this invention "modulation" of expression means either inhibition or stimulation; i.e., either a decrease or increase in expression. This modulation can be measured in ways which are routine in the art, for example by Northern blot assay of mRNA expression, or reverse transcriptase PCR, as taught in the examples of the instant application or by Western blot or ELISA assay of protein expression, or by an immunoprecipitation assay of protein expression. Effects on cell proliferation or tumor cell growth can also be measured, as taught in the examples of the instant application. Inhibition is presently a preferred form of modulation.

The oligonucleotides of this invention can be used in diagnostics, therapeutics, prophylaxis, and as research reagents and in kits. Since the oligonucleotides of this invention hybridize to nucleic acids encoding RPA70, sandwich, calorimetric and other assays can easily be constructed to exploit this fact. Provision of means for detecting hybridization of oligonucleotide with the RPA70 gene or mRNA can routinely be accomplished. Such provision may include enzyme conjugation, radiolabelling or any other suitable detection systems. Kits for detecting the presence or absence of variant forms of RPA70 may also be prepared.

The present invention is also suitable for diagnosing susceptibility to allele-specific treatment in patients suspected of having certain cancers. The ability of the oligonucleotides of the present invention to hybridize to RPA70 may be employed to diagnose such states. A number of assays may be formulated employing the present invention, which assays will commonly comprise contacting a tissue sample with an oligonucleotide of the invention under conditions selected to permit detection and, usually, quantitation of such inhibition. In the context of this invention, to "contact" tissues or cells with an oligonucleotide or oligonucleotides means to add the oligonucleotide(s), usually in a liquid carrier, to a cell suspension or tissue sample, either in vitro or ex vivo, or to administer the oligonucleotide(s) to cells or tissues within an animal.

The oligonucleotides of this invention may also be used for research purposes. For example, the function of a specific gene product in a signaling pathway may be investigated using specific oligonucleotides. Thus, the specific hybridization exhibited by the oligonucleotides may be used for assays, purifications, cellular product preparations and in other methodologies which may be appreciated by persons of ordinary skill in the art.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

The antisense compounds in accordance with this invention preferably comprise from about 5 to about 50 nucleobases. Particularly preferred are antisense oligonucleotides comprising from about 8 to about 30 nucleobases (i.e. from about 8 to about 30 linked nucleosides). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262. Further teaching of PNA compounds can be found in Nielsen et al. (*Science*, 1991, 254, 1497–1500).

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl, O-alkyl-O-alkyl, O-, S-, or N-alkenyl, or O-, S-, or N-alkynyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_2$ON($CH_3$)$_2$, O($CH_2$)$_n$$NH_2$, O($CH_2$)$_n$$CH_3$, O($CH_2$)$_n$O$NH_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, poly-alkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O-$CH_2CH_2OCH_3$, also known as 2'-O-(2-methoxyethyl) or 2'-MOE) (Martin et al., *Helv. Chim. Acta* 1995, 78, 486–504) i.e., an alkoxyalkoxy group. Further preferred modifications include 2'-dimethylaminooxyethoxy, i.e., a O($CH_2$)$_2$ON($CH_3$)$_2$ group, also known as 2'-DMAOE, and 2'-dimethylaminoethoxyethoxy (2'-DMAEOE) as described in examples hereinbelow.

Other preferred modifications include 2'-methoxy (2-O—$CH_3$), 2'-aminopropoxy (2'-O$CH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C or m5c), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the *Concise Encyclopedia Of polymer Science And Engineering* 1990, pages 858–859, Kroschwitz, J. I., ed. John Wiley & Sons, those disclosed by Englisch et al. (*Angewandte Chemie,* International Edition 1991, 30, 613–722), and those disclosed by Sanghvi, Y. S., Chapter 15, *Antisense Research and Applications* 1993, pages 289–302, Crooke, S. T. and Lebleu, B., ed., CRC press. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications* 1993, CRC press, Boca Raton, pages 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175, 273; 5,367,066; 5,432,272; 5,457,187; 5,459,255; 5,484, 908; 5,502,177; 5,525,711; 5,552,540; 5,587,469; 5,594, 121, 5,596,091; 5,614,617; and 5,681,941.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA* 1989, 86, 6553–6556), cholic acid (Manoharan et al., *Bioorg. Med. Chem. Lett.* 1994, 4, 1053–1059), a thioether, e.g., hexyl-S-tritylthiol (Manoharan et al., *Ann. N.Y. Acad. Sci.* 1992, 660, 306–309; Manoharan et al., *Bioorg. Med. Chem. Let.* 1993, 3, 2765–2770), a thiocholesterol (Oberhauser et al., *Nucl. Acids Res.* 1992, 20, 533–538), an aliphatic chain, e.g., dodecandiol or undecyl residues (Saison-Behmoaras et al., *EMBO J.* 1991, 10, 1111–1118; Kabanov et al., *FEBS Lett.* 1990, 259, 327–330; Svinarchuk et al., *Biochimie* 1993, 75, 49–54), a phospholipid, e.g., di-hexadecyl-rac-glycerol or triethylammonium 1,2-di-O-hexadecyl-rac-glycero-3-H-phosphonate (Manoharan et al., *Tetrahedron Lett.* 1995, 36, 3651–3654; Shea et al., *Nucl. Acids Res.* 1990, 18, 3777–3783), a polyamine or a polyethylene glycol chain (Manoharan et al., Nucleosides & Nucleotides 1995, 14, 969–973), or adamantane acetic acid (Manoharan et al., *Tetrahedron Lett.* 1995, 36, 3651–3654), a palmityl moiety (Mishra et al., *Biochim. Biophys. Acta* 1995, 1264, 229–237), or an octadecylamine or hexylamino-carbonyl-oxycholesterol moiety (Crooke et al., *J. pharmacol. Exp. Ther.,* 1996, 277, 923–937).

Representative United States patents that teach the preparation of such oligonucleotide conjugates include, but are not limited to, U.S. Pat. Nos. 4,828,979; 4,948,882; 5,218, 105; 5,525,465; 5,541,313; 5,545,730; 5,552,538; 5,578, 717, 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203; 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941.

The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques known in the art. This RNAse H-mediated cleavage of the RNA target is distinct from the use of ribozymes to cleave nucleic acids. Ribozymes are not comprehended by the present invention.

Examples of chimeric oligonucleotides include but are not limited to "gapmers," in which three distinct regions are present, normally with a central region flanked by two regions which are chemically equivalent to each other but distinct from the gap. A preferred example of a gapmer is an oligonucleotide in which a central portion (the "gap") of the oligonucleotide serves as a substrate for RNase H and is preferably composed of 2'-deoxynucleotides, while the flanking portions (the 5' and 3' "wings") are modified to have greater affinity for the target RNA molecule but are unable to support nuclease activity (e.g., fluoro- or 2'-O-methoxyethyl-substituted). Chimeric oligonucleotides are not limited to those with modifications on the sugar, but may also include oligonucleosides or oligonucleotides with modified backbones, e.g., with regions of phosphorothioate (P=S) and phosphodiester (P=O) backbone linkages or with regions of MMI and P=S backbone linkages. Other chimeras include "wingmers," also known in the art as "hemimers," that is, oligonucleotides with two distinct regions. In a preferred example of a wingmer, the 5' portion of the oligonucleotide serves as a substrate for RNase H and is preferably composed of 2'-deoxynucleotides, whereas the 3' portion is modified in such a fashion so as to have greater affinity for the target RNA molecule but is unable to support nuclease activity (e.g., 2'-fluoro- or 2'-O-methoxyethyl-substituted), or vice-versa. In one embodiment, the oligonucleotides of the present invention contain a 2'-O-methoxyethyl (2'-O-CH$_2$CH$_2$OCH$_3$) modification on the sugar moiety of at least one nucleotide. This modification has been shown to increase both affinity of the oligonucleotide for its target and nuclease resistance of the oligonucleotide. According to the invention, one, a plurality, or all of the nucleotide subunits of the oligonucleotides of the invention may bear a 2'-O-methoxyethyl (—O—CH$_2$CH OCH$_2$) modification. Oligonucleotides comprising a plurality of nucleotide subunits having a 2'-O-methoxyethyl modification can have such a modification on any of the nucleotide subunits within the oligonucleotide, and may be chimeric oligonucleotides. Aside from or in addition to 2'-O-methoxyethyl modifications, oligonucleotides containing other modifications which enhance antisense efficacy, potency or target affinity are also preferred. Chimeric oligonucleotides comprising one or more such modifications are presently preferred.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is well known to use similar techniques to prepare oligonucleotides such as the phosphorothioates and 2'-alkoxy or 2'-alkoxyalkoxy derivatives, including 2'-O-methoxyethyl oligonucleotides (Martin, P., *Helv. Chim. Acta* 1995, 78, 486–504). It is also well known to use similar techniques and commercially available modified amidites and controlled-pore glass (CPG) products such as biotin, fluorescein, acridine or psoralen-modified amidites and/or CPG (available from Glen Research, Sterling, Va.) to synthesize fluorescently labeled, biotinylated or other conjugated oligonucleotides.

The antisense compounds of the present invention include bioequivalent compounds, including pharmaceutically acceptable salts and prodrugs. This is intended to encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to pharmaceutically acceptable salts of the nucleic acids of the invention and prodrugs of such nucleic acids. "Pharmaceutically acceptable salts" are physiologically and pharmaceutically acceptable salts of the nucleic acids of the invention: i.e., salts that retain the desired biological activity of the parent compound and do not impart undesired toxicological effects thereto (see, for example, Berge et al., "Pharmaceutical Salts," *J. of Pharma Sci.* 1977, 66, 1–19).

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The oligonucleotides of the invention may additionally or alternatively be prepared to be delivered in a "prodrug" form. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993.

For therapeutic or prophylactic treatment, oligonucleotides are administered in accordance with this invention. Oligonucleotide compounds of the invention may be formulated in a pharmaceutical composition, which may include pharmaceutically acceptable carriers, thickeners, diluents, buffers, preservatives, surface active agents, neutral or cationic lipids, lipid complexes, liposomes, penetration enhancers, carrier compounds and other pharmaceutically acceptable carriers or excipients and the like in addition to the oligonucleotide. Such compositions and formulations are comprehended by the present invention.

Pharmaceutical compositions comprising the oligonucleotides of the present invention may include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., *Critical Reviews in Therapeutic Drug Carrier Systems* 1991, 8, 91–192; Muranishi, *Critical Reviews in Therapeutic Drug Carrier Systems* 1990, 7, 1–33). One or more penetration enhancers from one or more of these broad categories may be included.

Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arachidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.) (Lee et al., *Critical Reviews in Therapeutic Drug Carrier Systems* 1991, page 92; Muranishi, *Critical Reviews in Therapeutic Drug Carrier Systems* 1990, 7, 1; El-Hariri et al., *J. Pharm. pharmacol.* 1992 44, 651–654).

The physiological roles of bile include the facilitation of dispersion and absorption of lipids and fat-soluble vitamins (Brunton, Chapter 38 In: *Goodman & Gilman's The pharmacological Basis of Therapeutics,* 9th Ed., Hardman et al., eds., McGraw-Hill New York, N.Y., 1996, pages 934–935). Various natural bile salts, and their synthetic derivatives, act as penetration enhancers. Thus, the term "bile salt" includes any of the naturally occurring components of bile as well as any of their synthetic derivatives.

Complex formulations comprising one or more penetration enhancers may be used. For example, bile salts may be used in combination with fatty acids to make complex formulations.

Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) [Lee et al., *Critical Reviews in Therapeutic Drug Carrier Systems* 1991, page 92; Muranishi, *Critical Reviews in Therapeutic Drug Carrier Systems* 1990, 7, 1–33; Buur et al., *J. Control Rel.* 1990, 14, 43–51). Chelating agents have the added advantage of also serving as DNase inhibitors.

Surfactants include, for example, sodium lauryl sulfate, polyoxyethylene-9-lauryl ether and polyoxyethylene-20-cetyl ether (Lee et al., *Critical Reviews in Therapeutic Drug Carrier Systems* 1991, page 92); and perfluorochemical emulsions, such as FC-43 (Takahashi et al., *J. Pharm. phamacol.* 1988, 40, 252–57).

Non-surfactants include, for example, unsaturated cyclic ureas, 1-alkyl- and 1-alkenylazacyclo-alkanone derivatives (Lee et al., *Critical Reviews in Therapeutic Drug Carrier Systems* 1991, page 92); and non-steroidal anti-inflammatory agents such as diclofenac sodium, indomethacin and phenylbutazone (Yamashita et al., *J. Pharm. Pharmacol.* 1987, 39, 621–626).

As used herein, "carrier compound" refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. In contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinized maize starch, polyvinyl-pyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.). Sustained release oral delivery systems and/or enteric coatings for orally administered dosage forms are described in U.S. Pat. Nos. 4,704,295; 4,556,552; 4,309,406; and 4,309,404.

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

Regardless of the method by which the oligonucleotides of the invention are introduced into a patient, colloidal dispersion systems may be used as delivery vehicles to enhance the in vivo stability of the oligonucleotides and/or to target the oligonucleotides to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layers made up of lipids arranged in a bilayer configuration (see, generally, Chonn et al., *Current Op. Biotech.* 1995, 6, 698–708).

The pharmaceutical compositions of the present invention may be administered in a number of ways depending upon whether local or systemic treatment is desired and upon the area to be treated. Administration may be topical (including ophthalmic, vaginal, rectal, intranasal, epidermal, and transdermal), oral or parenteral. Parenteral administration includes intravenous drip, subcutaneous, intraperitoneal or intramuscular injection, pulmonary administration, e.g., by inhalation or insufflation, or intracranial, e.g., intrathecal or intraventricular, administration. Oligonucleotides with at least one 2'-O-methoxyethyl modification are believed to be particularly useful for oral administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral administration may include sterile aqueous solutions which may also contain buffers, diluents and other suitable additives. In some cases it may be more effective to treat a patient with an oligonucleotide of the invention in conjunction with other traditional therapeutic modalities in order to increase the efficacy of a treatment regimen. In the context of the invention, the term "treatment regimen" is meant to encompass therapeutic, palliative and prophylactic modalities. For example, a patient may be treated with conventional chemotherapeutic agents, particularly those used for tumor and cancer treatment. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide, trimetrexate, teniposide, cisplatin and diethylstilbestrol (DES). See, generally, *The Merck Manual of Diagnosis and Therapy*, 15th Ed. 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide).

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in vitro and in in vivo animal models. In general, dosage is from 0.01 μg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 μg to 100 g per kg of body weight, once or more daily, to once every 20 years.

Thus, in the context of this invention, by "therapeutically effective amount" is meant the amount of the compound which is required to have a therapeutic effect on the treated individual. This amount, which will be apparent to the skilled artisan, will depend upon the age and weight of the individual, the type of disease to be treated, perhaps even the gender and the genotype of the individual, and other factors which are routinely taken into consideration when designing a drug treatment. A therapeutic effect is assessed in the individual by measuring the effect of the compound on the disease state in the animal. For example, if the disease to be treated is cancer, therapeutic effects are assessed by measuring the rate of growth or the size of the tumor, or by measuring the production of compounds such as cytokines, production of which is an indication of the progress or regression of the tumor.

The following examples illustrate the present invention and are not intended to limit the same.

EXAMPLES

Example 1

Synthesis of Oligonucleotides

Unmodified oligodeoxynucleotides are synthesized on an automated DNA synthesizer (Applied Biosystems model 380B) using standard phosphoramidite chemistry with oxidation by iodine. β-cyanoethyldiisopropyl-phosphoramidites were purchased from Applied Biosystems (Foster City, Calif.). For phosphorothioate oligonucleotides, the standard oxidation bottle was replaced by a 0.2 M solution of $^3$H-1,2-benzodithiole-3-one 1,1-dioxide in acetonitrile for the stepwise thiation of the phosphite linkages. The thiation cycle wait step was increased to 68 seconds and was followed by the capping step. Cytosines may be 5-methyl cytosines. (5-methyl deoxycytidine phosphoramidites available from Glen Research, Sterling, Va. or Amersham Pharmacia Biotech, Piscataway, N.J.).

2'-methoxy oligonucleotides are synthesized using 2'-methoxy β-cyanoethyldiisopropyl-phosphoramidites (Chemgenes, Needham, Mass.) and the standard cycle for unmodified oligonucleotides, except the wait step after pulse delivery of tetrazole and base is increased to 360 seconds. Other 2'-alkoxy oligonucleotides are synthesized by a modification of this method, using appropriate 2'-modified amidites such as those available from Glen Research, Inc., Sterling, Va. 2'-fluoro oligonucleotides are synthesized as described in Kawasaki et al. (J. Med. Chem. 1993, 36, 831–841). Briefly, the protected nucleoside $N^6$-benzoyl-2'-deoxy-2'-fluoroadenosine is synthesized utilizing commercially available 9-β-D-arabinofuranosyladenine as starting material and by modifying literature procedures whereby the 2'-α-fluoro atom is introduced by a $S_N2$-displacement of a 2'-β-O-trifyl group. Thus $N^6$-benzoyl-9-β-D-arabinofuranosyladenine is selectively protected in moderate yield as the 3',5'-ditetrahydropyranyl (THP) intermediate. Deprotection of the THP and $N^6$-benzoyl groups is accomplished using standard methodologies and standard methods are used to obtain the 5'-dimethoxytrityl-(DMT) and 5'-DMT-3'-phosphoramidite intermediates.

The synthesis of 2'-deoxy-2'-fluoroguanosine is accomplished using tetraisopropyldisiloxanyl (TPDS) protected 9-β-D-arabinofuranosylguanine as starting material, and conversion to the intermediate diisobutyryl-arabinofuranosylguanosine. Deprotection of the TPDS group is followed by protection of the hydroxyl group with THP to give diisobutyryl di-THP protected arabinofuranosylguanine. Selective O-deacylation and triflation is followed by treatment of the crude product with fluoride, then deprotection of the THP groups. Standard methodologies are used to obtain the 5'-DMT- and 5'-DMT-3'-phosphoramidites.

Synthesis of 2'-deoxy-2'-fluorouridine is accomplished by the modification of a known procedure in which 2, 2'-anhydro-1-β-D-arabinofuranosyluracil is treated with 70% hydrogen fluoride-pyridine. Standard procedures are used to obtain the 5'-DMT and 5'-DMT-3'phosphoramidites.

2'-deoxy-2-fluorocytidine is synthesized via amination of 2'-deoxy-2-fluorouridine, followed by selective protection to give $N^4$-benzoyl-2'-deoxy-2'-fluorocytidine. Standard procedures are used to obtain the 5'-DMT and 5'-DMT-3'phosphoramidites.

2'-(2-methoxyethyl)-modified amidites are synthesized according to Martin, P. (Helv. Chim. Acta 1995, 78, 486–506). For ease of synthesis, the last nucleotide may be a deoxynucleotide. 2'-O-$CH_2CH_2OCH_3$-cytosines may be 5-methyl cytosines.

Synthesis of 5-Methyl cytosine monomers:

2,2'-Anhydro [1-(β-D-arabinofuranosyl)-5-methyluridine]:

5-Methyluridine (ribosylthymine, commercially available through Yamasa, Choshi, Japan) (72.0 g, 0.279 M), diphenyl-carbonate (90.0 g, 0.420 M) and sodium bicarbonate (2.0 g, 0.024 M) are added to DMF (300 mL). The mixture is heated to reflux, with stirring, allowing the evolved carbon dioxide gas to be released in a controlled manner. After 1 hour, the slightly darkened solution is concentrated under reduced pressure. The resulting syrup is poured into diethylether (2.5 L), with stirring. The product forms a gum. The ether is decanted and the residue is dissolved in a minimum amount of methanol (ca. 400 mL). The solution is poured into fresh ether (2.5 L) to yield a stiff gum. The ether is decanted and the gum is dried in a vacuum oven (60° C. at 1 mm Hg for 24 h) to give a solid which is crushed to a light tan powder (approximately 57 g, 85% crude yield). The material was used as is for further reactions.

2'-O-Methoxyethyl-5-methyluridine:

2,2'-Anhydro-5-methyluridine (195 g, 0.81 M), tris(2-methoxyethyl)boarate (231 g, 0.98 M) and 2-methoxyethanol (1.2 L) are added to a 2 L stainless steel pressure vessel and placed in a pre-heated oil bath at 160° C. After heating for 48 hours at 155–160° C., the vessel is opened and the solution evaporated to dryness and triturated with MeOH (200 mL). The residue is suspended in hot acetone (1 L). The insoluble salts are filtered, washed with acetone (150 mL) and the filtrate evaporated. The residue (280 g) is dissolved in $CH_3CN$ (600 mL) and evaporated. A silica gel column (3 kg) is packed in $CH_2Cl_2$/acetone/MeOH (20:5:3) containing 0.5% $Et_3NH$. The residue is dissolved in $CH_2Cl_2$ (250 mL) and adsorbed onto silica (150 g) prior to loading onto the column. The product is eluted with the packing solvent to give 160 g (63%) of product.

2'-O-Methoxyethyl-5'-O-dimethoxytrityl-5-methyluridine:

2'-O-Methoxyethyl-5-methyluridine (160 g, 0.506 M) is co-evaporated with pyridine (250 mL) and the dried residue dissolved in pyridine (1.3 L). A first aliquot of dimethoxytrityl chloride (94.3 g, 0.278 M) is added and the mixture stirred at room temperature for one hour. A second aliquot of dimethoxytrityl chloride (94.3 g, 0.278 M) is added and the reaction stirred for an additional one hour. Methanol (170 mL) is then added to stop the reaction. HPLC shows the presence of approximately 70% product. The solvent is evaporated and triturated with $CH_3CN$ (200 mL). The residue is dissolved in $CHCl_3$ (1.5 L) and extracted with 2×500 mL of saturated $NaHCO_3$ and 2×500 mL of saturated NaCl. The organic phase is dried over $Na_2SO_4$, filtered and evaporated. Approximately 275 g of residue is obtained. The residue is purified on a 3.5 kg silica gel column, packed and eluted with EtOAc/Hexane/Acetone (5:5:1) containing 0.5% $Et_3NH$. The pure fractions are evaporated to give approximately 164 g of product. Approximately 20 g additional is obtained from the impure fractions to give a total yield of approximately 183 g (57%).

3'-O-Acetyl-2'-O-methoxyethyl-5'-O-dimethoxytrityl-5-methyl-uridine:

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) are combined and stirred at room temperature for 24 hours. The reaction is monitored by tlc by first quenching the tlc sample with the addition of MeOH. Upon completion of the reaction, as judged by tlc, MeOH (50 mL) is added and the mixture evaporated at 35° C. The residue is dissolved in $CHCl_3$ (800 mL) and extracted with 2×200 mL of saturated sodium bicarbonate and 2×200 mL of saturated NaCl. The water layers are back extracted with 200 mL of $CHCl_3$. The combined organics are dried with sodium sulfate and evaporated to give 122 g of residue (approx. 90% product). The residue is purified on a 3.5 kg silica gel column and eluted using EtOAc/Hexane(4:1). Pure product fractions are evaporated to yield approximately 96 g (84%).

3'-O-Acetyl-2'-O-methoxyethyl-5'-O-dimethoxytrityl-5-methyl-4- triazoleuridine:

A first solution is prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) is added to a solution of triazole (90 g, 1.3 M) in $CH_3CN$ (1 L), cooled to −5° C. and stirred for 0.5 h using an overhead stirrer. $POCl_3$ is added dropwise, over a 30 minute period, to the stirred solution maintained at 0–10° C., and the resulting mixture stirred for an additional 2 hours. The first solution is added dropwise, over a 45 minute period, to the later solution. The resulting reaction mixture is stored overnight in a cold room. Salts are filtered from the reaction mixture and the solution is evaporated. The residue is dissolved in EtOAc (1 L) and the insoluble solids are removed by filtration. The filtrate is washed with 1×300 mL of $NaHCO_3$ and 2×300 mL of saturated NaCl, dried over sodium sulfate and evaporated. The residue is triturated with EtOAc to give the title compound.

2'-O-Methoxyethyl-5'-O-dimethoxytrityl-5-methylcytidine:

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) is stirred at room temperature for 2 hours. The dioxane solution is evaporated and the residue azeotroped with MeOH (2×200 mL). The residue is dissolved in MeOH (300 mL) and transferred to a 2 liter stainless steel pressure vessel. MeOH (400 mL) saturated with $NH_3$ gas is added and the vessel heated to 100° C. for 2 hours (tlc shows complete conversion). The vessel contents are evaporated to dryness and the residue is dissolved in EtOAc (500 mL) and washed once with saturated NaCl (200 mL). The organics are dried over sodium sulfate and the solvent is evaporated to give 85 g (95%) of the title compound.

$N^4$-Benzoyl-2'-O-methoxyethyl-5'-O-dimethoxytrityl-5-methyl-cytidine:

2'-O-Methoxyethyl-5'-O-dimethoxytrityl-5-methylcytidine (85 g, 0.134 M) is dissolved in DMF (800 mL) and benzoic anhydride (37.2 g, 0.165 M) is added with stirring. After stirring for 3 hours, tlc shows the reaction to be approximately 95% complete. The solvent is evaporated and the residue azeotroped with MeOH (200 mL). The residue is dissolved in $CHCl_3$ (700 mL) and extracted with saturated $NaHCO_3$ (2×300 mL) and saturated NaCl (2×300 mL), dried over $MgSO_4$ and evaporated to give a residue (96 g). The residue is chromatographed on a 1.5 kg silica column using EtOAc/Hexane (1:1) containing 0.5% $Et_3NH$ as the eluting solvent. The pure product fractions are evaporated to give approximately 90 g (90%) of the title compound.

$N^4$-Benzoyl-2'-O-methoxyethyl-5'-O-dimethoxytrityl-5-methylcytidine-3'-amidite:

$N^4$-Benzoyl-2'-O-methoxyethyl-5'-O-dimethoxytrityl-5-methylcytidine (74 g, 0.10 M) is dissolved in $CH_2Cl_2$ (1 L). Tetrazole diisopropylamine (7.1 g) and 2-cyanoethoxy-tetra-(isopropyl)phosphite (40.5 mL, 0.123 M) are added with stirring, under a nitrogen atmosphere. The resulting mixture is stirred for 20 hours at room temperature (tlc shows the reaction to be 95% complete). The reaction mixture is extracted with saturated $NaHCO_3$ (1×300 mL) and saturated NaCl (3×300 mL). The aqueous washes are back-extracted with $CH_2Cl_2$ (300 mL), and the extracts are combined, dried over $MgSO_4$ and concentrated. The residue obtained is chromatographed on a 1.5 kg silica column using EtOAc/Hexane (3:1) as the eluting solvent. The pure fractions are combined to give 90.6 g (87%) of the title compound.

5-methyl-2'-deoxycytidine (5-me-C) containing oligonucleotides are synthesized according to published methods (Sanghvi et al., *Nucl. Acids Res.* 1993, 21, 3197–3203) using commercially available phosphoramidites (Glen Research, Sterling Va. or ChemGenes, Needham Mass.).

2'-O-(dimethylaminooxyethyl) nucleoside amidites

2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-$O^2$-2'-anhydro-5-methyluridine $O^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) are dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) is added in one portion. The reaction is stirred for 16 h at ambient temperature. TLC (Rf 0.22, ethyl acetate) indicates a complete reaction. The solution is concentrated under reduced pressure to a thick oil. This is partitioned between dichloromethane (1 L) and saturated sodium bicarbonate (2×1 L) and brine (1 L). The organic layer is dried over sodium sulfate and concentrated under reduced pressure to a thick oil. The oil is dissolved in a 1:1 mixture of ethyl acetate and ethyl ether (600 mL) and the solution is cooled to −10° C. The resulting crystalline product is collected by filtration, washed with ethyl ether (3×200 mL) and dried (40° C., 1 mm Hg, 24 h) to approximately 149 g (74.8%) of white solid. TLC and NMR are consistent with pure product.

5'-O-tert-Butyldiphenylsilyl-2'-O-(2-hydroxyethyl)-5-methyluridine

In a 2 L stainless steel, unstirred pressure reactor is added borane in tetrahydrofuran (1.0 M, 2.0 eq, 622 mL). In the fume hood and with manual stirring, ethylene glycol (350 mL, excess) is added cautiously at first until the evolution of hydrogen gas subsides. 5'-O-tert-Butyldiphenylsilyl-$O^2$-2'-anhydro-5-methyluridine (149 g, 0.311 mol) and sodium bicarbonate (0.074 g, 0.003 eq) are added with manual stirring. The reactor is sealed and heated in an oil bath until an internal temperature of 160° C. is reached and then maintained for 16 h (pressure<100 psig). The reaction vessel is cooled to ambient and opened. TLC (Rf 0.67 for desired product and Rf 0.82 for ara-T side product, ethyl acetate) indicates about 70% conversion to the product. In order to avoid additional side product formation, the reaction is stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue is purified by column chromatography (2 kg silica gel, ethyl acetate-hexanes gradient 1:1 to 4:1). The appropriate fractions are combined, stripped and dried to product as a white crisp foam (approximately 84 g, 50%), contaminated starting material (approximately 17.4 g) and pure reusable starting material (approximately 20 g). The yield based on starting material less pure recovered starting material is approximately 58%. TLC and NMR are consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) is mixed with triphenylphosphine (11.63 g, 44.36 mmol) and N-hydroxyphthalimide (7.24 g, 44.36 mmol). It is then dried over $P_2O_5$ under high vacuum for two days at 40° C. The reaction mixture is flushed with argon and dry THF (369.8 mL, Aldrich, sure seal bottle) is added to get a clear solution. Diethyl-azodicarboxylate (6.98 mL, 44.36 mmol) is added dropwise to the reaction mixture. The rate of addition is maintained such that resulting deep red coloration is just discharged before adding the next drop. After the addition is complete, the reaction is stirred for 4 hrs. By that time TLC shows the completion of the reaction (ethylacetate:hexane, 60:40). The solvent is evaporated in vacuum. Residue obtained is placed on a flash column and eluted with ethyl acetate:hexane (60:40), to get 2'-O-([2-phthalimidoxy) ethyl]-5'-t-butyldiphenylsilyl-5-methyluridine as white foam (21.819, 86%).

5'-O-tert-butyldiphenylsilyl-2'-O-[(2-formadoximinooxy) ethyl]-5-methyluridine

2'-O-([2-phthalimidoxy)ethyl]-5'-t-butyldiphenylsilyl-5-methyluridine (3.1 g, 4.5 mmol) is dissolved in dry $CH_2Cl_2$ (4.5 mL) and methylhydrazine (300 mL, 4.64 mmol) is added dropwise at −10° C. to 0° C. After 1 hr the mixture is filtered, the filtrate is washed with ice cold $CH_2Cl_2$ and the combined organic phase is washed with water, brine and dried over anhydrous $Na_2SO_4$. The solution is concentrated to get 2'-O-(aminooxyethyl) thymidine, which is then dissolved in MeOH (67.5 mL). To this formaldehyde (20% aqueous solution, w/w, 1.1 eg.) is added and the mixture for 1 hr. Solvent is removed under vacuum; residue chromatographed to get 5'-O-tert-butyldiphenylsilyl-2'-O-[(2-formadoximinooxy) ethyl]-5-methyluridine as white foam (approximately 1.95, 78%).

5'-O-tert-Butyldiphenylsilyl-2'-O-[N,N-dimethylaminooxyethyl]-5-methyluridine

5'-O-tert-butyldiphenylsilyl-2'-O-[(2-formadoximinooxy) ethyl]-5-methyluridine (1.77 g, 3.12 mmol) is dissolved in a solution of 1 M pyridinium p-toluenesulfonate (PPTS) in dry MeOH (30.6 mL). Sodium cyanoborohydride (0.39 g, 6.13 mmol) is added to this solution at 10° 1 C. under inert atmosphere. The reaction mixture is stirred for 10 minutes at 10° C. After that the reaction vessel is removed from the ice bath and stirred at room temperature for 2 hr, the reaction monitored by TLC (5% MeOH in $CH_2Cl_2$). Aqueous $NaHCO_3$ solution (5%, 10 mL) is added and extracted with ethyl acetate (2×20 mL). Ethyl acetate phase is dried over anhydrous $Na_2SO_4$, evaporated to dryness. Residue is dissolved in a solution of 1 M PPTS in MeOH (30.6 mL). Formaldehyde (20% w/w, 30 mL, 3.37 mmol) is added and the reaction mixture is stirred at room temperature for 10 minutes. Reaction mixture is cooled to 10° C. in an ice bath, sodium cyanoborohydride (0.39 g, 6.13 mmol) is added and reaction mixture stirred at 10° C. for 10 minutes. After 10 minutes, the reaction mixture is removed from the ice bath and stirred at room temperature for 2 hrs. To the reaction mixture 5% $NaHCO_3$ (25 mL) solution is added and extracted with ethyl acetate (2×25 mL). Ethyl acetate layer is dried over anhydrous $Na_2SO_4$ and evaporated to dryness. The residue obtained is purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (approximately 14.6 g, 80%).

2'-O-(dimethylaminooxyethyl)-5-methyluridine

Triethylamine trihydrofluoride (3.9 mL, 24.0 mmol) is dissolved in dry THF and triethylamine (1.67 mL, 12 mmol, dry, kept over KOH). This mixture of triethylamine-2HF is then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction is monitored by TLC (5% MeOH in $CH_2Cl_2$). Solvent is removed under vacuum and the residue placed on a flash column and eluted with 10% MeOH in $CH_2Cl_2$ to get 2'-O-(dimethylaminooxyethyl)-5-methyluridine (approximately 766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) is dried over $P_2O_5$ under high vacuum overnight at 40° C. It is then co-evaporated with anhydrous pyridine (20 mL). The residue obtained is dissolved in pyridine (11 mL) under argon atmosphere. 4-dimethylaminopyridine (26.5 mg, 2.60 mmol), 4,4'-dimethoxytrityl chloride (880 mg, 2.60 mmol) is added to the mixture and the reaction mixture is stirred at room temperature until all of the starting material disappeared. Pyridine is removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (approximately 1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) is co-evaporated with toluene (20 mL). To the residue N,N-diisopropylamine tetrazonide (0.29 g, 1.67 mmol) is added and dried over $P_2O_5$ under high vacuum overnight at 40° C. Then the reaction mixture is dissolved in anhydrous acetonitrile (8.4 mL) and 2-cyanoethyl-N,N,$N^1$,$N^1$-tetraisopropylphosphoramidite (2.12 mL, 6.08 mmol) is added. The reaction mixture is stirred at ambient temperature for 4 hrs under inert atmosphere. The progress of the reaction is monitored by TLC (hexane:ethyl acetate 1:1). The solvent is evaporated, then the residue is dissolved in ethyl acetate (70 mL) and washed with 5% aqueous $NaHCO_3$ (40 mL). Ethyl acetate layer is dried over anhydrous $Na_2SO_4$ and concentrated. Residue obtained is chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (approximately 1.04 g, 74.9%).

2'-dimethylaminoethoxyethoxy (2'-DMAEOE) nucleoside amidites

2'-dimethylaminoethoxyethoxy (2'-DMAEOE) nucleoside amidites (also known in the art as 2'-O-dimethylaminoethoxyethyl) or 2'-DMAEOE nucleoside amidites) are prepared as follows. Other nucleoside amidites are prepared similarly.

2'-O-[2(2-N,N-dimethylaminoethoxy)ethyl]-5-methyl uridine

2[2-(Dimethylamino)ethoxy]ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. $O^2$-2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-[2(2-N,N-dimethylaminoethoxy)ethyl]-5-methyl uridine

To 0.5 g (1.3 mmol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with $CH_2Cl_2$ (2×200 mL). The combined $CH_2Cl_2$ layers are washed with saturated $NaHCO_3$ solution, followed by saturated NaCl solution and dried over anhydrous sodium sulfate. Evaporation of the solvent followed by silica gel chromatography using MeOH:$CH_2Cl_2$:$Et_3N$ (20:1, v/v, with 1% triethylamine) gives the title compound.

5'-O-Dimethoxytrityl-2'-O-[2(2-N,N-dimethylaminoethoxy)ethyl)]-5-methyl uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylamino-ethoxy)ethyl)]-5-methyluridine (2.17 g, 3 mmol) dissolved in $CH_2Cl_2$ (20 mL) under an atmosphere of argon. The reaction mixture is stirred overnight and the solvent evaporated. The resulting residue is purified by silica gel flash column chromatography with ethyl acetate as the eluent to give the title compound.

Oligonucleotides having methylene(methylimino) (MMI) backbones are synthesized according to U.S. Pat. No. 5,378,825, which is coassigned to the assignee of the present invention and is incorporated herein in its entirety. For ease of synthesis, various nucleoside dimers containing MMI linkages were synthesized and incorporated into oligonucleotides. Other nitrogen-containing backbones are synthesized according to WO 92/20823 which is also coassigned to the assignee of the present invention and incorporated herein in its entirety.

Oligonucleotides having amide backbones are synthesized according to De Mesmaeker et al. (*Acc. Chem. Res.* 1995, 28, 366–374). The amide moiety is readily accessible by simple and well-known synthetic methods and is compatible with the conditions required for solid phase synthesis of oligonucleotides.

Oligonucleotides with morpholino backbones are synthesized according to U.S. Pat. No. 5,034,506 (Summerton and Weller).

Peptide-nucleic acid (PNA) oligomers are synthesized according to P. E. Nielsen et al. (*Science* 1991, 254, 1497–1500).

After cleavage from the controlled pore glass column (Applied Biosystems) and deblocking in concentrated ammonium hydroxide at 55° C. for 18 hours, the oligonucleotides were purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}P$ nuclear magnetic resonance spectroscopy, and for some studies oligonucleotides were purified by HPLC, as described by Chiang et al. (*J. Biol. Chem.* 1991, 266, 18162). Results obtained with HPLC-purified material were similar to those obtained with non-HPLC purified material.

Example 2

Analysis of Variant Sequences in Human RPA70 and Loss Of Heterozygosity

PCR single-strand conformation polymorphism (PCR-SSCP)analysis was used to detect DNA sequence variances in the RPA70 gene. Total RNA was isolated from 36 lymphoblast cell lines derived from 36 normal, unrelated individuals. cDNA was synthesized and analyzed for variances using PCR-SSCP as described (Iwahana, H., et al., BioTechniques, 1992, 12, 64–66; Liu, Q. and Sommer, S. S., BioTechniques, 1995, 18, 470). Changes in DNA sequence were confirmed by standard DNA sequencing methods.

Analysis of 36 unrelated individuals using single strand conformation polymorphism and sequencing revealed that RPA70 mRNA contains 5 high frequency polymorphisms or variances with heterozygosity frequency ranging from 25% to 42% (see Table 1). One of the five variances, at nucleotide 1120, codes for an alternative amino acid at position 351 of RPA70 (threonine to alanine).

For Loss of Heterozygosity (LOH) analysis, at least 180 breast, colon, ovarian and non-small cell lung cancers were retrieved from archived pathological specimens at the Uppsala Pathology Institute in Sweden. All specimens were derived from individuals of Swedish decent. Analysis was performed as described here and in Sjogren et al. (J. Natl. Cancer Inst., 1996, 88, 173–182). Tumor tissue was microdissected from normal tissue, and tumor DNA from informative patients (heterozygotes at nucleotide 1120 of RPA70) was amplified using PCR. Finally, a quantitative sequencing reaction using pharmacia's Autoload and Alfexpress DNA Sequencer was performed to determine the degree of LOH. Sequencing reactions were standardized with a set of mixed DNA solutions differing in allele proportions. Peak analysis was performed using Fragment Manager (Pharmacia Biotech).

LOH at the RPA70 locus was determined for 189 paired normal and cancer tissues from patients selected for constitutional RPA70 heterozygosity. LOH for RPA70 was shown to be 44% for colon cancer, 58% for ovarian cancer, 19.5% for breast cancer, and 27% for non-small cell lung carcinoma.

TABLE 1

Variance in the RPA70 Gene and Loss of Heterozygosity

| Position | Region | Variance | AA change | Heterozygosity |
|---|---|---|---|---|
| 81 | coding | G -> A | silent | 26% |
| 1120 | coding | A -> G | thr -> ala | 25% |
| 1674 | coding | T -> C | silent | 31% |
| 2050 | 3'-UTR | T -> C | n/a | 42% |
| 2297 | 3'-UTR | $C_9 -> C_8$ | n/a | 33% |

Example 3

Design and Testing of Human RPA70 Antisense Oligonucleotide Sequences

Antisense oligonucleotides were used to demonstrate that inhibition of RPA70 leads to inhibition of cell survival, and that RPA70 is indeed an essential gene in human cells. Antisense oligonucleotides targeted to human RPA70 were designed and synthesized as phosphorothioate oligodeoxynucleotides according to Example 1; oligonucleotide sequences are presented in Table 2. Human RPA70 sequence data are from the Human replication protein A 70 kDa subunit cDNA sequence published by Erdile, L. F., et al. (J. Biol. Chem., 1991, 266, 12090–12098); Genbank accession number M63488. This sequence is provided herein as SEQ ID NO: 1. Oligonucleotides, ISIS 12781, ISIS 12786, ISIS 12791, ISIS 13085 and VAR 13085 (a truncated version of ISIS 13085) were design to target segments of RPA70 mRNA that contain variances and were designed so that the polymorphic nucleotide was opposite position 9 (VAR 13085), position 10 (ISIS 12786) or position 11 (ISIS 12781, ISIS 12791 and ISIS 13085) of the oligonucleotide.

TABLE 2

Oligonucleotide Sequences Targeted to Human RPA70

| OLIGO NO. | NUCLEOTIDE SEQUENCE[1] (5' -> 3') | SEQ ID NO: | TARGET GENE NUCLEOTIDE COORDINATES[2] | GENE TARGET REGION |
|---|---|---|---|---|
| ISIS 12778 | CCCACCCGGGTCCCGCGCCG | 3 | 0001–0020 | 5'-UTR |
| ISIS 12779 | GACCATGGCTCCACCGCCAA | 4 | 0056–0075 | AUG |
| ISIS 12780 | TGGCCGACCATGGCTCCACC | 5 | 0061–0080 | AUG |
| ISIS 12781 | TAGCTTCAGCAGACTCCTGG | 6 | 1665–1684 | coding |
| ISIS 12782 | TGATGCTCATGACCAGCCTT | 7 | 1881–1900 | coding |
| ISIS 12783 | ACTGCTCCTCTCACATCAAT | 8 | 1911–1930 | STOP |
| ISIS 12784 | GATTCCATTCTGCCTATTTG | 9 | 1951–1970 | 3'-UTR |

TABLE 2-continued

Oligonucleotide Sequences Targeted to Human RPA70

| OLIGO NO. | NUCLEOTIDE SEQUENCE[1] (5' -> 3') | SEQ ID NO: | TARGET GENE NUCLEOTIDE COORDINATES[2] | GENE TARGET REGION |
|---|---|---|---|---|
| ISIS 12785 | CTGCACTGTGTAGCTAACAT | 10 | 2001–2020 | 3'-UTR |
| ISIS 12786 | GCACGAGGGAGGAAATTGCT | 11 | 2041–2060 | 3'-UTR |
| ISIS 12787 | GAGCGTATTTTCCTTTGCCT | 12 | 2080–2099 | 3'-UTR |
| ISIS 12788 | CAGAGGGAGTGACTGGTCTT | 13 | 2155–2174 | 3'-UTR |
| ISIS 12789 | TGACTTACGACATAATTCCT | 14 | 2210–2229 | 3'-UTR |
| ISIS 12790 | TGGTCTGCAGTTAGGGTCAG | 15 | 2230–2249 | 3'-UTR |
| ISIS 12791 | ATGGGGGGGGTGGTCACCA | 16 | 2287–2306 | 3'-UTR |
| ISIS 13085 | TAGCTTCAGCGGACTCCTGG | 17 | 1665–1684[3] | coding |
| VAR 13085 | GCTTCAGCGGACTCCTGG | 18 | 1665–1682[3] | coding |

[1]All linkages are phosphorothioate linkages.
[2]Co-ordinate from Genbank Accession No. M63488, locus name "HUMRPA70KD", SEQ ID NO. 1.
[3]Emboldened nucleotide co-ordinates indicate a variant specific oligonucleotide.

The human tumor cell lines Mia Paca II, T24, SW480, A549, and HeLa were obtained from the American Type Culture Collection (Manassas, Va.) and cultured as recommended by supplier. All media were supplemented with 10% (vol/vol) heat inactivated fetal bovine serum (JRH Biosciences, Lenexa, Kans.), 100 µg/ml penicillin-streptomycin (Life Technologies) and 2 mM L-glutamine (Life Technologies). All cell lines were grown under 5% $CO_2$/95% air in a humidified incubator at 37° C.

Antisense treatments were performed with phosphorothioate oligodeoxynucleotides. Cells were cultured in 6-well plates to 60–80% confluency for use in oligonucleotide treatments. Cells were washed once with OPTI-MEM™ (Life Technologies), pre-warmed to 37° C. Transfections were carried out in 1 ml OPTI-MEM™ containing 3 µg LIPOFECTIN™ (Life Technologies) per ml of Opti-MEM™ per 100 nM added oligonucleotide. OPTI-MEM™ containing the appropriate amount of LIPOFECTIN™ was added to the cells followed by addition of oligonucleotides from 1000×stocks. (For dose-response studies oligonucleotides were added from 20×stocks.) Cells were incubated for 5 h at 37° C. Following treatment, medium was removed and replaced with pre-warmed replete media (Bennett, C. F., et al., *Mol. Pharm.*, 1992, 41, 1023–1033; Monia, B. P., et al., *Nature Medicine*, 1993, 2, 668–674).

Target mRNA levels were assessed by Northern blotting with target specific random primed [α-$^{32}$P]dCTP-labeled cDNA probes, as described below. cDNAs for probes were obtained by specific RT-PCR of cellular RNAs.

For determination of mRNA levels by Northern blot, total RNA was prepared from cells 24 h after oligonucleotide addition using a SDS-lysis method (Peppel, K. and Baglioni, C., *Biotechniques*, 1990, 9, 711–713). Northern analysis was performed as described (Brown, T. and Mackey, K., in *Current protocols in Molecular Biology* (Ausubel, F. ed.), 1987, Vol. 1, pp. 4.9.1–4.912, Greene publishing, New York). To determine RPA70 mRNA expression RNA blots were probed using a random primed [α-$^{32}$P]dCTP-labeled cDNA probe corresponding to a 562 nucleotide sequence (1519–2081) from human RPA70 (Erdile, L. F., et al., *J. Biol. Chem.*, 1991, 266, 12090–12098). After transfer, membranes were prehybridized with Quik-Hyb solution (Stratagene, La Jolla, Calif.) for 1 h at 68° C. and then hybridized 1–4 hours with 12.5×10$^6$ cpm of cDNA probe and 2 µg salmon sperm DNA carrier in a total of 10 ml of hybridization solution. Following hybridization, membranes were washed twice at room temperature for 15 min in 2×SSC/0.1% SDS and then once at 60° C. for 30 min in 0.1×SSC/0.1% SDS.

RNA on the blots was quantified by phosphorimaging on a Fuji FLA-2000. RPA70 mRNA levels are normalized to the level of RPA70 mRNA measured in cells treated with 400 nM control 20N-mer phosphorothioate oligonucleotide and expressed as percentage of control treated levels. Glyceraldehyde phosphate dehydrogenase (GAPDH) mRNA levels were probed using a random primed GAPDH cDNA generated by RT-PCR with human GAPDH primers (Stratagene, Inc., La Jolla, Calif.).

To assess the ability of these oligonucleotides to inhibit RPA70 expression, A549 cells were treated with oligonucleotide at 400 nM in the presence of LIPOFECTIN™, and the level of RPA70 mRNA was measured by Northern blot analysis (see Table 3). Most oligonucleotides reduced RPA70 mRNA levels by 50% to 94%. The most potent oligonucleotide, ISIS 12790, reduced RPA70 mRNA levels by 94%. This oligonucleotide targets a non-variant region located in the 3'-UTR of RPA70 mRNA and is not variance-specific. The most potent oligonucleotide targeting a variance was ISIS 12781, which resulted in ~75% reduction in RPA70 mRNA levels.

TABLE 3

Inhibition of RPA70 mRNA expression in human A549 cells by RPA70 antisense phosphorothioate oligodeoxynucleotides

| ISIS No: | SEQ ID NO: | GENE TARGET REGION | % mRNA EXPRESSION | % mRNA INHIBITION |
|---|---|---|---|---|
| basal | — | — | 100% | 0% |
| 12778 | 3 | 5'-UTR | 21% | 0.79 |
| 12779 | 4 | AUG | 0.35 | 0.65 |
| 12780 | 5 | AUG | 0.18 | 82% |
| 12781 | 6 | coding | 0.24 | 0.76 |
| 12782 | 7 | coding | 0.08 | 0.92 |
| 12783 | 8 | STOP | 0.28 | 0.72 |
| 12784 | 9 | 3'-UTR | 0.43 | 0.57 |
| 12785 | 10 | 3'-UTR | 0.2 | 0.8 |
| 12786 | 11 | 3'-UTR | 0.73 | 0.27 |
| 12787 | 12 | 3'-UTR | 0.18 | 0.82 |
| 12788 | 13 | 3'-UTR | 0.43 | 0.57 |
| 12789 | 14 | 3'-UTR | 0.62 | 0.38 |
| 12790 | 15 | 3'-UTR | 0.06 | 0.94 |
| 12791 | 16 | 3'-UTR | 0.88 | 0.12 |

To determine the effects of ISIS 12790 on tumor cell survival, T24, A549, Mia Paca II, and SW480 cells were treated with either ISIS 12790 or ISIS 13706 (a 20-mer with identical nucleotide composition but containing 7 mismatches relative to the target) and surviving cells counted 72 hours later.

Cells were transfected with matched, mismatched, or non-allele specific anti-RPA70 (ISIS 12790) oligonucleotides as described above. Following transfection, the cells were allowed to recover either three days (HeLa cells) or 6 days (Mia Paca II cells). The number of cells remaining attached to the tissue culture dish was quantified by Sulforhodamine B (SRB) staining (FluoReporter Colorimetric Cell Protein Assay Kit, Molecular probes).

For experiments where cell number was measured directly by hemocytometer, cells were plated in six well dishes 24 hr prior to the experiment and transfected at approximately 50–70% confluency with various phosphorothioate oligonucleotides at 400 nM, as described above. Following a single transfection, the cells were allowed to recover 72 hours. After 72 hr the cells were washed, trypsinized, and cell number was determined by hemocytometer. For each experiment, treatments were performed in triplicate wells. The number of cells corresponding to each well was determined twice.

Statistical analysis of mRNA levels and cell survival data were performed using BMDP Statistical package, Version 7.0 (BMDP Statistical Software, Inc., Los Angeles, Calif.). Data were subjected to ANOVA and the results were expressed in terms of F-values, t-values, and significance. For cell survival data, analyses included repeated measurements with 3 between factors (drug, concentration, and position). For mRNA levels only the 3 between factors were considered. Global comparisons were performed with F-tests and pairwise comparisons with t-tests. In each case, since there was no interaction with position, results were pooled and analyzed with two between factors (drug and concentration). Treatment with ISIS 12790 was associated with decreased cell number in all four tumor cell lines (see Table 4). The decrease in cell number observed in T24 cells was 79%. The decrease observed in the other three cell lines was: A549, 98% decrease; Mia Paca II, 85% decrease; SW480, 81% decrease. These data demonstrate that inhibition of RPA70 with antisense oligonucleotides is associated with a decrease in cell survival, confirming that this gene is essential for survival of the four tumor lines examined.

TABLE 4

Inhibition of RPA70 mRNA expression by ISIS 12790 in various tumor cell lines

| Tumor Cell line | % Cell Survival | % Cell Killing |
|---|---|---|
| T24 | 0.21 | 0.79 |
| A549 | 0.02 | 0.98 |
| Mia Paca II | 0.15 | 0.85 |
| SW480 | 0.19 | 81% |

Example 4

Variance-specific suppression of cell survival

Two phosphorothioate oligodeoxynucleotides, designed to target the variant sequences at position 1674 of the RPA70 mRNA were synthesized. ISIS 12781 was complementary to the T variance at position 1674. VAR 13085 was complementary to the C at position 1674, but was reduced in length relative to ISIS 12781 by the removal of 2 nucleotides from the 5' end of the oligonucleotide. Shortening the length of the oligonucleotide enhanced oligonucleotide discrimination between the two variant alleles.

Several cell lines were genotyped for the variance at position 1674 to identify cell lines expressing only one variant form of the gene. Mia Paca II cells were found to express only the C allele of RPA70, while A549 and HeLa cells expressed only the T allele.

Treatment of HeLa cells with ISIS 12781, which matches the target gene in these cells, resulted in a statistically significant dose-dependent inhibition of RPA70 mRNA expression over a concentration range between 50 nM and 400 nM ($p<0.001$). The total phosphorothioate oligonucleotide concentration was held constant at 400 nM by supplementing the tested oligonucleotide to 400 nM with the 20N-mer randomized oligonucleotide. This control oligonucleotide was synthesized by incorporation of all 4 bases in equal proportions at each position of the 20-mer. Results are shown in Table 5. The IC50 for inhibiting expression of RPA70 was between 50 nM and 100 nM. In contrast, treatment of these cells with VAR 13085, which contains a single mismatch to the target in these cells, had only a small effect on the level of mRNA, even at 400 nM. As a positive control, cells were treated with ISIS 12790. This oligonucleotide targets a different site within the gene and is not variance-specific. Treatment of the cells with ISIS 12790 resulted in a dose-dependent decrease of RPA70 mRNA levels with maximum suppression of mRNA levels occurring at 200 nM and an IC50 of less than 50 nM. None of the oligonucleotides inhibited the level of GAPDH mRNA significantly in HeLa cells.

TABLE 5

Dose Response of RPA70 mRNA Expression in HeLa Cells to RPA70 Antisense Phosphorothioate Oligodeoxynucleotides

| ISIS # | SEQ ID NO: | ASO Gene Target | Dose | % mRNA Expression | % mRNA Inhibition |
|---|---|---|---|---|---|
| basal | — | — | — | 1 | — |
| 12781 | 6 | coding | 50 nM | 0.61 | 0.39 |
| " | " | " | 100 nM | 0.36 | 0.64 |
| " | " | " | 200 nM | 0.36 | 0.64 |

TABLE 5-continued

Dose Response of RPA70 mRNA Expression in HeLa Cells to RPA70 Antisense Phosphorothioate Oligodeoxynucleotides

| ISIS # | SEQ ID NO: | ASO Gene Target | Dose | % mRNA Expression | % mRNA Inhibition |
|---|---|---|---|---|---|
| " | " | " | 400 nM | 0.27 | 0.73 |
| 12790 | 15 | 3'-UTR | 50 nM | 0.29 | 0.71 |
| " | " | " | 100 nM | 0.15 | 0.85 |
| " | " | " | 200 nM | 0.1 | 0.9 |
| " | " | " | 400 nM | 0.14 | 0.86 |
| 13085 | 17 | coding | 50 nM | 1.31 | — |
| " | " | " | 100 nM | 1.35 | — |
| " | " | " | 200 nM | 0.81 | 0.19 |
| " | " | " | 400 nM | 0.74 | 0.26 |

Treatment of Mia Paca II cells with increasing concentrations of VAR 13085, which matches the target gene in these cells, resulted in a statistically significant dose-dependent decrease in the level of RPA70 mRNA compared to mismatched oligonucleotide (p=0.002). Results are shown in Table 6. This effect was not observed when VAR 13085 was applied to HeLa cells. Treatment of Mia Paca II cells with ISIS 12781, which contains a single mismatch from the target in these cells, had little effect on the level of RPA70 mRNA. ISIS 12790 resulted in a dose-dependent decrease in RPA70 mRNA levels quantitatively similar to the effect observed with this oligonucleotide in HeLa cells. None of the oligonucleotides inhibited the level of GAPDH mRNA significantly in Mia Paca II cells.

TABLE 6

Dose Response of RPA70 mRNA Expression Mia Paca II Cells to RPA70 Antisense Phosphorothioate Oligodeoxynucleotides

| ISIS # | SEQ ID NO: | ASO Gene Target | Dose | % mRNA Expression | % mRNA Inhibition |
|---|---|---|---|---|---|
| basal | — | — | — | 1 | — |
| 12781 | 6 | coding | 50 nM | 0.79 | 0.21 |
| " | " | " | 100 nM | 0.83 | 0.17 |
| " | " | " | 200 nM | 0.72 | 0.18 |
| " | " | " | 400 nM | 0.81 | 0.19 |
| 12790 | 15 | 3'-UTR | 50 nM | 0.43 | 0.57 |
| " | " | " | 100 nM | 0.18 | 0.82 |
| " | " | " | 200 nM | 0.14 | 0.86 |
| " | " | " | 400 nM | 0.2 | 0.8 |
| 13085 | 17 | coding | 50 nM | 0.7 | 0.3 |
| " | " | " | 100 nM | 0.58 | 0.42 |
| " | " | " | 200 nM | 0.37 | 0.63 |
| " | " | " | 400 nM | 0.27 | 0.73 |

To determine the effect of variance-specific antisense oligonucleotides on cell survival, cells were treated with oligonucleotides and cell survival measured by Sulforhodamine B staining. Treatment of HeLa cells with increasing concentrations of the matched antisense oligonucleotide, ISIS 12781, resulted in a statistically significant dose-dependent decrease in cell survival compared to mismatched oligonucleotide (p<0.001), with an IC50 between 100 nM and 200 nM. At the maximum concentration of ISIS 12781, 400 nM, there was an 84% reduction of surviving cells. Treatment with VAR 13085, which contains a single base mismatch relative to the allele expressed in HeLa cells, resulted in little change in cell survival. After treatment with 400 nM oligonucleotide, the amount of cells remaining with VAR 13085 was 3.1-fold higher than with ISIS 12781. Treatment of cells with the non-allele specific anti-RPA70 oligonucleotide, ISIS 12790, caused a dose-dependent reduction in the number of surviving cells, with a 90% reduction in the number of surviving cells at 400 nM. The IC50 for the decrease was less than 100 nM. The IC50s for inhibition of HeLa cell survival correlated with the IC50s for RPA70 mRNA suppression by both ISIS 12781 and ISIS 12790 oligonucleotides.

TABLE 7

Dose Response of HeLa Cell Survival to RPA70 Antisense Phosphorothioate Oligodeoxynucleotides

| ISIS # | SEQ ID NO: | ASO Gene Target | Dose | % Cell Survival | % Cell Killing |
|---|---|---|---|---|---|
| basal | — | — | — | 1 | — |
| 12781 | 6 | coding | 50 nm | 0.8 | 0.2 |
| " | " | " | 100 nM | 0.56 | 0.44 |
| " | " | " | 100 nM | 0.22 | 0.44 |
| " | " | " | 400 nM | 0.16 | 0.84 |
| 12790 | 15 | 3'-UTR | 50 nM | 0.23 | 0.77 |
| " | " | " | 100 nM | 0.34 | 0.66 |
| " | " | " | 200 nM | 0.11 | 0.89 |
| " | " | " | 400 nM | 0.11 | 0.89 |
| 13085 | 17 | coding | 50 nM | 83% | 0.17 |
| " | " | " | 100 nM | 0.88 | 0.12 |
| " | " | " | 200 nM | 0.63 | 0.37 |
| " | " | " | 400 nM | 0.5 | 0.5 |

Treatment of Mia Paca II cells with the matched antisense oligonucleotide, VAR 13085, resulted in a dose-dependent decrease in cell survival with an IC50 between 100 nM and 200 nM (FIG. 5B) and a 90% reduction in the number of surviving cells at 400 nM. Inhibition of cell survival was seen also with 100 and 200 nM of the mismatched oligonucleotide ISIS 12781. However, at 400 nM, there was a statistically significant difference in survival with less survival seen in cells treated with the matched oligonucleotide, VAR 13085, than the mismatched oligonucleotide, ISIS 12781 (p=0.02). At 400 nM, there was a 4.6 fold difference in cell survival between matched and mismatched oligonucleotides. As with HeLa cells, treatment of the Mia Paca II cells with increasing concentrations of ISIS 12790 yielded a dose-dependent decrease in the number of surviving cells, with an IC50 of less than 100 nM. The IC50 for inhibition of Mia Paca II cell survival was similar to that for suppression of RPA70 mRNA for both VAR 13085 and ISIS 12790. The effect of antisense treatment on cell survival for both cell lines appears to be cytotoxic rather than cytostatic as the absolute number of cells decreases for both cell lines when treated with matched antisense oligonucleotides. For each of the cell lines, the successful inhibition of RPA70 expression and cell survival by two distinct oligonucleotides targeting different sites in the mRNA, strongly suggests that inhibition of cell survival is target dependent and acts through an antisense mechanism.

TABLE 8

Dose Response of Mia Paca II Cell Survival to RPA70 Antisense Phosphorothioate Oligodeoxynucleotides

| ISIS # | SEQ ID NO: | ASO Gene Target | Dose | % Cell Survival | % Cell Killing |
|---|---|---|---|---|---|
| basal | — | — | — | 1 | — |
| 12781 | 6 | coding | 50 nm | 0.87 | 0.13 |
| " | " | " | 100 nM | 0.51 | 0.49 |
| " | " | " | 200 nM | 0.42 | 0.58 |
| " | " | " | 400 nM | 0.44 | 0.56 |
| 12790 | 15 | 3'-UTR | 50 nM | 0.61 | 0.39 |
| " | " | " | 100 nM | 0.14 | 0.86 |

TABLE 8-continued

Dose Response of Mia Paca II Cell Survival to RPA70 Antisense Phosphorothioate Oligodeoxynucleotides

| ISIS # | SEQ ID NO: | ASO Gene Target | Dose | % Cell Survival | % Cell Killing |
|---|---|---|---|---|---|
| " | " | " | 200 nM | 0.06 | 0.94 |
| " | " | " | 400 nM | 0.12 | 0.88 |
| 13085 | 17 | coding | 50 nM | 0.87 | 0.13 |
| " | " | " | 100 nM | 0.62 | 0.38 |
| " | " | " | 200 nM | 0.23 | 0.77 |
| " | " | " | 400 nM | 0.09 | 91% |

Example 5

Effects of ISIS 12790 on Mia Paca II tumors in NMRI mice

Studies were carried out to determine the effect of ISIS 12790 (SEQ ID NO. 15), a non-allele specific RPA70 antisense oligonucleotide, on tumor size and weight in vivo. NMRI nu/nu mice (B&K Universal, Fremont, Calif.) were injected with $10^6$ Mia Paca II cells (grown as described in Example 3) in 300 µl MATRIGEL® matrix (Becton Dickinson, Franklin Lakes, N.J.). After one week of tumor growth, the mice were given an ALZET® osmotic minipump model 1002 (Alza Corporation, Newark, Del.) containing oligonucleotide or saline. Delivery of oligonucleotide was continuous for 14 days. The dosage of oligonucleotide was 10 mg/kg/day. Each sample set contained three mice. Tumor volume was measured regularly and after two weeks, the tumors were taken out and weighed.

Results for tumor volume are shown in Table 9. The average final weights of the tumors were 297 mg for the saline control, and 161 mg for ISIS 12790 (SEQ ID NO. 15). ISIS 12790 (SEQ ID NO. 15) delayed tumor progression over the two week period compared to a saline control and inhibited tumor growth by approximately 40%. Results with the scrambled control oligonucleotide, ISIS 13706, gave similar results to the saline control.

TABLE 9

Effect of ISIS 12790 on tumor volume in NMRI mice

| ISIS # | SEQ ID NO: | ASO Gene Target | Days | Tumor volume (mm³) |
|---|---|---|---|---|
| saline | — | — | 0 | 134 |
| " | " | " | 1 | 275 |
| " | " | " | 2 | 335 |
| " | " | " | 6 | 401 |
| " | " | " | 7 | 422 |
| " | " | " | 9 | 570 |
| " | " | " | 13 | 597 |
| " | " | " | 14 | 557 |
| 12790 | 15 | 3'-UTR | 0 | 134 |
| " | " | " | 1 | 186 |
| " | " | " | 2 | 220 |
| " | " | " | 6 | 252 |
| " | " | " | 7 | 290 |
| " | " | " | 9 | 370 |
| " | " | " | 13 | 358 |
| " | " | " | 14 | 331 |

What is claimed is:

1. An antisense compound 8 to 30 nucleobases in length targeted to a nucleic acid encoding the human Replication Protein A p70 subunit, wherein said antisense compound inhibits the expression of the human Replication Protein A p70 subunit.

2. The antisense compound of claim 1 which is an antisense oligonucleotide.

3. The antisense compound of claim 1 comprising at least an 8-nucleobase portion of SEQ ID NO: 3, 4, 5, 6, 7, 8, 9, 10, 12, 13, 15 or 18.

4. The antisense compound of claim 2 which comprises at least one modified internucleoside linkage.

5. The antisense compound of claim 4 wherein the modified internucleoside linkage is a phosphorothioate linkage.

6. The antisense compound of claim 2 which comprises at least one modified sugar moiety.

7. The antisense compound of claim 6 wherein the modified sugar moiety is a 2'-O-methoxyethyl sugar moiety.

8. The antisense compound of claim 2 which comprises at least one modified nucleobase.

9. The antisense compound of claim 8 wherein the modified nucleobase is a 5-methylcytosine.

10. A composition comprising the antisense compound of claim 1 and a pharmaceutically acceptable carrier or diluent.

11. The composition of claim 10 further comprising a colloidal dispersion system.

12. The composition of claim 10 wherein the antisense compound is an antisense oligonucleotide.

13. A method of inhibiting the expression of the human Replication protein A p70 subunit comprising contacting tissues or cells which express said human Replication protein A p70 subunit in vitro with an effective amount of the antisense compound of claim 1 whereby expression of the human Replication protein A p70 subunit is inhibited.

* * * * *